(12) United States Patent
Missotten et al.

(10) Patent No.: US 8,045,168 B2
(45) Date of Patent: Oct. 25, 2011

(54) APPARATUS AND METHOD FOR ANALYSING THE COMPOSITION OF CROP IN A CROP-CONVEYING MACHINE

(75) Inventors: Bart M. A. Missotten, Herent (BE); Lodewijk J. G. Claessens, Wageningen (NL); Koen O. G. Maertens, Oostduinkerke (BE); Pál Jancsók, Strassen (LU)

(73) Assignee: CNH America LLC, New Holland, PA (US)

( * ) Notice: Subject to any disclaimer, the term of this patent is extended or adjusted under 35 U.S.C. 154(b) by 634 days.

(21) Appl. No.: 11/658,373

(22) PCT Filed: Jul. 26, 2005

(86) PCT No.: PCT/EP2005/053650
§ 371 (c)(1),
(2), (4) Date: Jun. 8, 2009

(87) PCT Pub. No.: WO2006/010761
PCT Pub. Date: Feb. 2, 2006

(65) Prior Publication Data
US 2009/0258684 A1  Oct. 15, 2009

(30) Foreign Application Priority Data
Jul. 28, 2004 (GB) .................................. 0416766.4

(51) Int. Cl.
*G01N 21/55* (2006.01)

(52) U.S. Cl. ........................................ 356/445; 356/448
(58) Field of Classification Search .......... 356/445–448, 356/52–68, 407–408, 411, 413, 414; 250/226, 250/200, 216; 209/580, 581, 582, 509, 552, 209/576, 577; 56/10.2 C, 10.2 R
See application file for complete search history.

(56) References Cited

U.S. PATENT DOCUMENTS
4,259,020 A * 3/1981 Babb ............................ 356/402
* cited by examiner

*Primary Examiner* — Tri T Ton
(74) *Attorney, Agent, or Firm* — Michael G. Harms; Patrick M. Sheldrake (57) ABSTRACT

An apparatus is provided for analysing the composition of crop in a crop-conveying machine, such as a harvesting machine. The crop in the machine is conveyed along a crop movement path, whereof a portion is illuminated by a light source (23). A camera (24) captures sequential images of crop in the crop movement path. The apparatus further comprises a control device and a processing device operatively connected to the camera and light source. The intensity and/or the colour of light output by the light source (23) is adjustable in dependence on one or more control commands generated by the control device and determined by optical characteristics generated by the processing device from one or more prior images captured by the camera (24). A portion of the image may include a reference member (26) adjacent the crop movement path.

37 Claims, 8 Drawing Sheets

APPARATUS AND METHOD FOR ANALYSING THE COMPOSITION OF CROP IN A CROP-CONVEYING MACHINE

This invention relates to an apparatus and a method for analysing the composition of crop in a crop-conveying machine.

An example of such a machine is a combine harvester. Other machines in which the apparatus and method of the invention find application, include but are not limited to, crop handling and/or storage apparatuses such as silos, grain tankers, rail vehicles, ship holds, containers and weighing devices.

Such apparatuses are typically characterised by the presence of a path along which crop is caused to move (herein a "crop movement path") by conveying elements such as scoops, augers, belts and shakers.

It is for various reasons strongly desirable to analyse the composition of crop moving along such movement paths.

By "composition of crop" and "crop composition" are meant the proportion of intact crop relative to damaged crop, straw, weed seeds, chaff, insects and/or other contaminants moving in the movement path.

The aforementioned contaminants are referred to herein as "material other than grain" or "MOG" for convenience. It is however to be understood that the invention is not applicable solely to crops that have granular form. On the contrary the invention is of use in connection with numerous non-grain crops such as, but not limited to, chopped forage material, harvested cotton, grapes, and small bulk harvested fruits (berries).

One reason it is desirable to analyse the composition of crop relates to the valuation of the crop.

When crop is conveyed in crop movement paths as aforesaid, very often an assumption is made that the crop is pure and free of contaminants. However this is rarely the case. Therefore any valuation of the crop based for example solely on the mass or volume of the crop may be inaccurate and may in any event be iniquitous since different batches of the crop might contain different amounts and types of MOG.

Moreover there is a general desire on the part of farmers, food companies and crop wholesalers to acquire data on the yields of crop available from certain sources, and make comparisons and/or adjustments of the growing process in dependence on such data.

Yet a further reason for analysing the composition of crop concerns the conditions prevailing during harvesting.

In the case of use of a combine harvester, after threshing and separating the grains from the harvested stalks the grain passes via a so-called "clean grain elevator" and "bubble-up auger" to a clean grain store (i.e. a large tank located to the rear of the driver's cab on the vehicle).

Hitherto generally the only tests carried out on the grain in the clean grain elevator relate to the total mass or volume of crop passing via the elevator at a given moment (for yield mapping purposes); and moisture tests aimed at establishing the moisture content of the crop. The objective of the latter measurement is, primarily, to predict the mass of the crop after it has undergone a drying process (thereby producing a normalised crop mass indication).

However a real time indication of the proportion of MOG and broken grains in the clean grain elevator could enable the operator of the combine harvester to adjust for example his thresher speed, concave clearance, fan speed, upper and lower sieve opening, harvesting speed and/or the height of the header bar of the harvester in order to minimise the amount of MOG and broken kernels entering the clean grain tank and thereby improve the efficiency of the harvesting operation.

As an alternative to operator intervention aimed at improving harvesting efficiency, the result of a real time crop composition analysis could be used as an input to a vehicle control arrangement that automatically adjusts the various working parts of the machine, without the need for operator judgement.

Various machine vision apparatuses aimed at providing crop composition analysis have been proposed in the prior art.

EP-A-0 826 959 discloses a fruit harvesting machine including a machine vision apparatus for determining the amount of non-fruit matter in a fruit crop passing through the machine.

The apparatus of EP-A-0 826 959 includes a camera and illumination source that are directed towards fruit collected in a bin. The camera captures an initial image of the crop, and a processor connected thereto assigns to each pixel of the image one of two extreme greyscale levels (corresponding respectively to the presence of fruit and contaminants) determined by the initial greyscale level of the pixel relative to an automatically adjustable threshold value. Thereafter the processor records the number of pixels of at least one of the extreme greyscale values and establishes from the recorded value the ratio of the fruit to contaminants in the image.

Thus EP-A-0 826 959 discloses a form of threshold adjustment and manipulation of the recorded image.

Following such analysis the software disclosed in EP-A-0 826 959 adjusts a parameter of the harvesting machine, e.g., its forward speed, in order to minimise the presence of non-fruit contaminants.

EP-A-0 826 959 also discloses erosion and dilation techniques aimed at improving the quality of discrimination between fruit and contaminants.

The apparatus and method of EP-A-0 826 959 are highly successful when the crop under consideration is fruit such as grapes. This is partly because, for particular wavelengths, the differences in reflectivity between most tree-borne fruits on the one hand and contaminants such as twigs, leaves, buds and shoots on the other are very pronounced. Therefore it is possible to make use of the aforementioned greyscale differences in an effective manner.

In this imaging system, the reflection under infrared light depends on the water and sugar contents of the crop material.

However, not all harvested crops are so easily distinguished using the greyscale techniques disclosed in EP-A-0 826 959.

For example, when harvesting grains the likely contaminants include broken grains, straw, chaff and dust each of which has a moisture content and reflectance characteristic similar to that of the crop (grain) for the wavelengths proposed in EP-A-0 826 959.

Therefore there is a need for a machine vision apparatus and method that are applicable in the harvesting of grains as well as fruit.

Moreover the environment within a grain harvesting machine such as a combine harvester is extremely harsh. Therefore there is a need for considerable robustness in apparatus used for discriminating between grains and contaminants.

Thus some other prior art machine vision apparatuses, such as those disclosed in *Estimation of Weight Percentage of Scabby Wheat Kernels Using an Automatic Machine Vision and Neural Network Base I System*—Ruan et al Transaction of ASAE Vol. 44 (4) 983-988; *A Computer Vision System for Rice Kernel Quality Evaluation* by Yun et al 2002 ASAE Annual International Meeting; and See *Sorting by Machine*

Vision by Berlage et al Agricultural Engineering, October 1984 probably are sufficiently robust only to be reliable in laboratory tests, and not in field-based vehicles. Moreover these publications describe no procedure to monitor MOG content but discriminate between grains of different crops or different grain qualities from the same crop.

U.S. Pat. No. 6,452,157 describes an apparatus comprising a camera for detecting foreign bodies in fibre material, such as cotton. The apparatus is used in a unit, which scans tufts of cotton fibres and elects tufts of a deviating colour. The colour of the light source may be set manually or automatically, from the colours detected by the camera. This apparatus does not analyse the crop composition in each tuft, it only reacts to sudden colour changes between tufts.

The principle of adjusting a setting of a parameter of a harvesting machine is also disclosed in U.S. Pat. No. 6,119,442; whereas U.S. Pat. No. 6,421,990 and U.S. Pat. No. 6,449,932 disclose arrangements in which particular characteristics of crop particles or grains are sensed using machine vision and other sensing apparatuses. However it is believed that the arrangements of the aforementioned US patent publications are sub-optimal bearing in mind the technical problems specified hereinabove.

SUMMARY OF THE INVENTION

Thus according to the invention in a first aspect there is provided apparatus for analysing the composition of crop in a crop-conveying machine, the apparatus comprising a conveyor for conveying crop in the machine, the conveyor comprising a portion defining a crop movement path; a light source that illuminates crop in the crop movement path; a camera that captures sequential images of crop in the crop movement path; a control device; and a processing device all operatively connected together, the intensity and/or the colour of light output by the light source being adjustable in dependence on one or more control commands generated by the control device and determined by optical characteristics generated by the processing device of one or more prior images captured by the camera, characterised in that the processing device is configured for measuring the reflectance of each element of the image at least two wavelengths and carrying out at least one of an addition, a subtraction, a multiplication or a division of the measured reflectance values of each said image element for better discrimination between crop components.

An advantage of this arrangement is to permit optimisation of the illumination conditions for the crop according to one or more predetermined criteria such as, but not limited to, the type of crop. Consequently the light source may be of a comparatively low level of precision in terms of its emitted light energy or colour (frequency), while still (over a sequence of two or more images) providing a good level of accuracy of the analysis. Therefore the light source may be of lower cost than those proposed in the prior art arrangements. Furthermore it may be of a type that is sufficiently robust as to withstand the harsh conditions encountered for example in the grain elevator of a combine harvester.

Initial settings of the light source may be derived from the crop information provided by the operator.

Preferably the apparatus includes a reference member, the colour properties of which are known, located in or adjacent the crop movement path so as to appear in the images captured by the camera, the processor being capable of assessing the colour characteristics of the reference member and in dependence thereon generating the aforesaid control commands.

Although this feature is known per se its use in a machine vision apparatus using comparatively low precision illumination means is novel and offers particular advantages. Principal among these is that the combination effectively enhances the precision of the apparatus without the need for light sources whose hue, intensity and colour balance are controllable with high accuracy over a prolonged period.

This is of particular importance, since even when driven by a voltage-stabilised driver the colour characteristics of the outputs of some light sources tend to vary over time. Furthermore such drift of the outputs of such sources is unlikely to be the same for each of three sources of different primary colours. The use of a stabilisation arrangement that adjusts the outputs in dependence on preceding images offsets such disadvantages of (generally comparatively cheap) illumination components that suffer from drift.

Conveniently the known colour properties of the reference member include its reflectance at one or more predetermined wavelengths.

It is also preferable that the light source includes respective red, green and blue light emitting diodes (LED's). Violet and near-infrared LEDs can be added for widening the analysis range of the apparatus. For instance, the reflection of the light inside of broken grain kernel is very outspoken when compared the reflection of the untouched kernel surface. Near-infrared analysis highlights the presence of moisture and protein. Violet and ultraviolet highlight the presence of sugar and starch.

The use of such LEDs is associated with cost advantages. This is partly because they are readily available from numerous suppliers. Also there is no need for complicated control circuits for such devices, since the drivers available for LED devices are widely available and have in recent years been simplified to a great extent.

Moreover, LEDs are generally adequately robust to survive for a long time the dusty, high-vibration environments encountered in combine harvesters, grain silos, hoppers, vehicles such as rail cars and tankers and in ships.

Preferably the said predetermined wavelengths include the respective wavelengths corresponding generally to the peak wavelength outputs of the red, green and blue and possibly other LEDs respectively.

Matching the reflection of the reference member at least approximately to the peak wavelengths output by the LEDs advantageously enhances the extent to which the apparatus of the invention is able to compensate for drift in the LED outputs.

In a preferred embodiment of the invention the reference member is an elongate strip that in use of the apparatus is aligned with and adjacent an edge of each image captured by the camera.

This feature advantageously allows the use of a reference member without significantly adversely affecting the image area available for the analysis of crop composition. It can happen that the illumination is not the same at the side of the image. However the side is practical because the grains at the side of the window are not necessarily touching the glass such that the quality of those pixels is low. Rather than using the edge area for a low-quality grain analysis, it therefore can advantageously be used for application of the reference member.

Conveniently the processing device is programmable and is programmed to carry out one or more of:
 a threshold adjustment;
 an erosion adjustment; and/or
 a dilation adjustment
on one or more said images captured by the camera.

These per se known techniques advantageously assist in the accurate determination of the composition of the crop moving in the crop movement path.

In preferred embodiments of the apparatus of the invention the camera is so located as to capture images of crop moving in the clean grain elevator or in a bypass system thereof, of a combine harvester, whereby the said elevator itself or the bypass defines the crop movement path.

Hitherto there has been no reliable, low cost arrangement using machine vision for assessing in real time the composition of crop in a combine harvester. The arrangement of the invention obviates this disadvantage.

Preferably the apparatus of the invention includes a housing containing the camera and having formed therein a window permitting light reflected from crop moving in the crop movement path to impinge on the camera for the capturing of the said images. Also, optionally, the housing contains the light source, the light from which illuminates the crop via the window.

These features advantageously assist the apparatus of the invention to withstand the harsh conditions encountered in crop processing and/or handling machinery.

The apparatus of the invention may also optionally include one or more of a moisture sensor, a protein or oil content sensor and/or a level sensor operatively connected to the processing device. The output from the device processing the images can be used for validating or adjusting the output generated by other sensors, such as the moisture or protein or oil content sensor, such that data can be generated which relate to the crop itself and not to the MOG.

These optional features are of particular benefit when the apparatus is installed in a harvesting machine such as a combine harvester.

The apparatus of the invention may preferably include a display device operatively connected to the processing device and located so as to be visible to an operator. The processing device may be programmable and programmed to cause the display device to display one or more images captured by the camera. Conveniently the processing device causes the display device to display the said images sequentially in real time.

Thus through use of the apparatus it is possible to provide a practical, real-time image of crop being harvested in a harvesting machine, while at the same time allowing automated adjustment of one or more machine parameters based on an electronic analysis of the composition of the crop.

Conveniently the processing device causes the display device to display the said images following one or more of:
  a threshold adjustment;
  an erosion adjustment; and/or
  a dilation adjustment carried out on each said image.

Thus the real-time images may undergo processing that makes the diverse components of the crop moving in the crop movement path readily discernible to the operator.

The apparatus may also be such that the processing device generates one or more commands causing the display device to display data pertaining to the composition of the crop.

Thus if desired the operator may augment the knowledge gained from the real time images by data displayed e.g. in numerical, bar chart or other graphical forms or by indication on the image itself.

According to a second aspect of the invention there is provided a method of analysing the composition of crop in a crop-conveying machine, the method comprising the steps of:
  causing the crop to move along a crop movement path;
  illuminating the crop in the said path by means of an adjustable source of illumination; and
  operating a camera to capture a series of real time images of the crop;
  operating a processing device to cause adjustment of the illumination source in dependence on one or more optical characteristics of one or more prior images of the crop captured by the camera,
  characterised in that it comprises the further step of:
  measuring the reflectance of each element of the image at least two wavelengths and carrying out at least one of an addition, a subtraction, a multiplication or a division of the measured reflectance values of each said image element for better discrimination between crop components.

The calculated values may have more discerning power for grain and DOG components than the reflectance value for a single wavelength.

This method may advantageously be practised using an apparatus according to the first aspect of the invention disclosed herein. It is however possible to practise the method using other apparatuses if desired.

Conveniently the step of operating a processing device to cause adjustment of the illumination source includes the step of comparing the optical characteristics of a reference member with optical characteristics of crop captured in one or more said prior images.

The step of illuminating the crop optionally but desirably includes illuminating the crop by means of each of a red, a green and a blue light source. This advantageously means that all components of e.g. a granular crop are identifiable using the method of the invention. Violet or ultra-violet and near-infrared light sources can be added for further analysis of the crop components and detection of MOG.

Conveniently the step of operating a processing device to cause adjustment of the illumination source includes respective adjustment, as necessary, of each respective said light source. Such adjustments need not take place simultaneously.

It is also preferable that the method of the invention includes the step of displaying one or more said images via a display device. Also preferably the method includes the step of displaying data characteristic of the crop moving in the crop movement path via a display device.

The advantages of such displaying are as set out hereinabove.

The method of the invention also optionally includes the step of carrying out one or more of:
  a threshold adjustment;
  an erosion adjustment; and/or
  a dilation adjustment
on one or more said images captured by the camera.

This aspect of the method advantageously allows improvement of the accuracy of the method in identifying the components of crop using per se known techniques. Such techniques are cheap to implement using robust apparatus components.

Further, preferred aspects of the method of the invention include:
  the step of carrying out a threshold adjustment, by detecting the grey level of each pixel of an initial image containing no grain and allocating to it an extreme grey level depending on whether its grey level is greater or less than a predetermined threshold value;
  the step of automatically carrying out the threshold adjustment; and/or
  the step of dividing each image into a plurality of image portions; and separately processing each image portion.

When the method includes the step of automatically carrying out the threshold adjustment the latter optionally includes recording the number of pixels of the initial image having a predetermined grey level; establishing from the recording two peak greyscale values and from the said peak values establishing a minimum value that defines the threshold.

BRIEF DESCRIPTION OF THE DRAWINGS

There now follows a description of preferred embodiments of the invention, by way of non-limiting example, with reference being made to the accompanying drawings in which.

DETAILED DESCRIPTION

Commonly, when referring to material processed by a combine harvester, the terms "grain", "straw", and "tailings" are used. The terms "chaff" and "broken grains" are also relevant to the invention disclosed herein. These terms are not limiting.

"Grain" refers to that part of the crop which is threshed and separated from the discardable part of the crop material. The latter is referred to as MOG (Material Other than Grain), comprising "straw" and "chaff". Incompletely threshed ears are referred to as "tailings".

The terms "forward", "rearward", "upper", "lower", "left", "right", etc when used in connection with a combine harvester and/or components thereof are determined with reference to the combine harvester in its normal operational condition and may refer either to the direction of forward operative travel of the combine harvester or to the direction of normal material flow through components thereof. Such terms should not be construed as limiting.

Referring to the drawings, the clean grain elevator 10 of a combine harvester comprises a paddle conveyor 11 having a series of flat or concave paddles 12 (represented schematically in FIGS. 1 and 2) secured in a linear series to a flexible drive chain 13 and arranged in an elevator housing having a rectangular cross-section.

Chain 13 is an endless, ovaloid loop that at its respective ends (not visible in the drawings) is wrapped around respective sprockets that are driveably rotatable under power taken off from the transmission system of the combine harvester. The sprockets are controlled to drive the chain 13 so that the paddles 12 travel a vertically extending, ovaloid path along the walls of the elevator housing.

At the lowermost end of this path the paddles 12 pass through a trough at the bottom of the grain cleaning mechanism of the combine harvester thereby repeatedly picking up portions of cleaned crop. The motion of the paddles 12 on the chain 13 conveys the portions along the grain entrance 14 of a housing 19 comprising an auger 16, which constitutes a bypass which receives crop portions from the paddles 12. The return auger 16 contains an auger member 17 which conveys the grain upwardly to a grain exit 18 whence the grain falls into the return run of the elevator 10.

Thus the conveying apparatus of the combine harvester involves a split elevation of cleaned grains. The main path is the travel of the grains on the paddles from the grain cleaning mechanism to the grain entrance of the bubble-up auger (not shown). The second path is the downward fall through the housing 19 and the upward conveyance via the auger 16 to the return run of the elevator and therefrom back to the main path.

Figure 1:
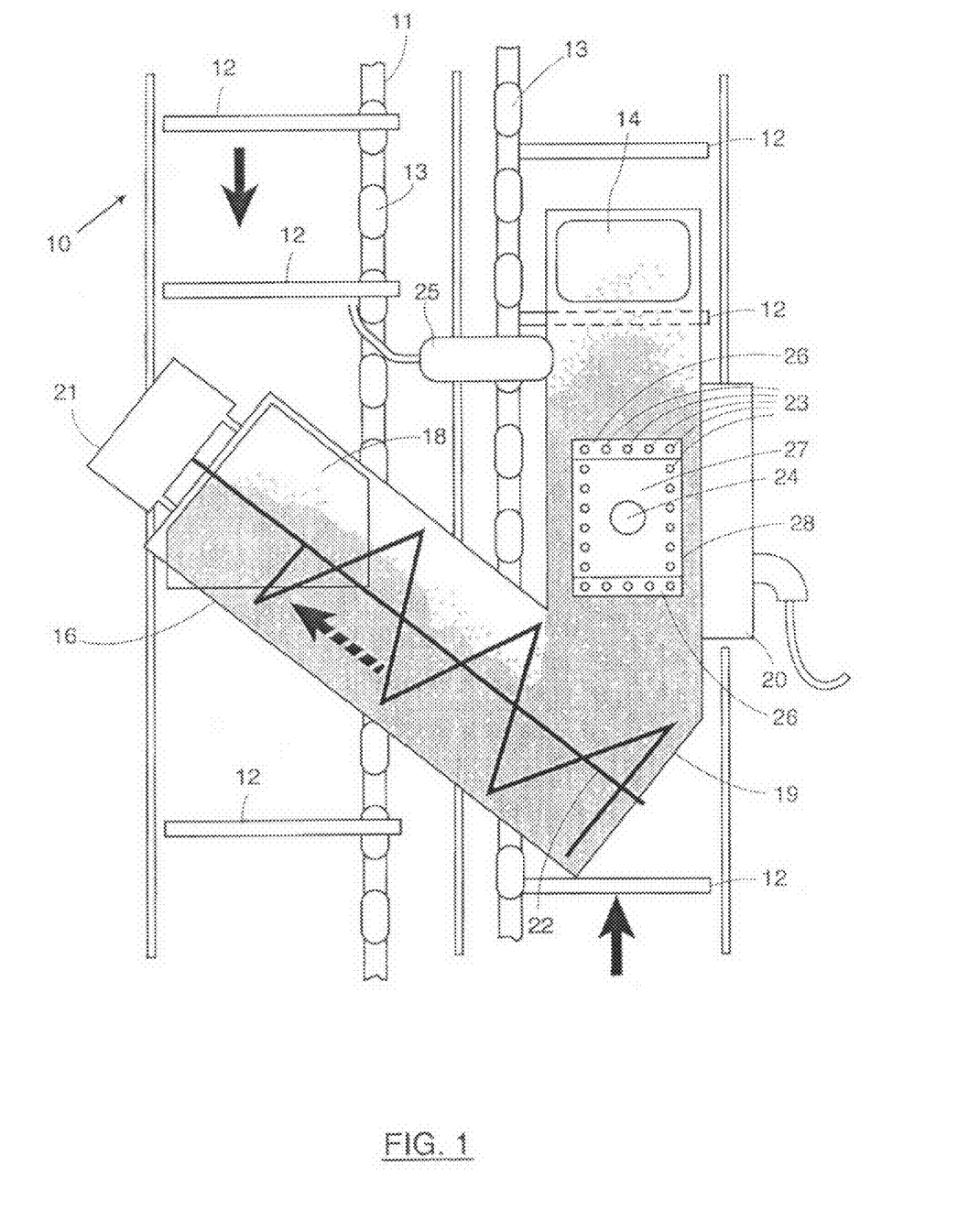
FIG. 1 is a schematic elevational view from one direction of a clean grain elevator and return auger of a combine harvester and showing the location of apparatus according to the invention.
Figure 2:
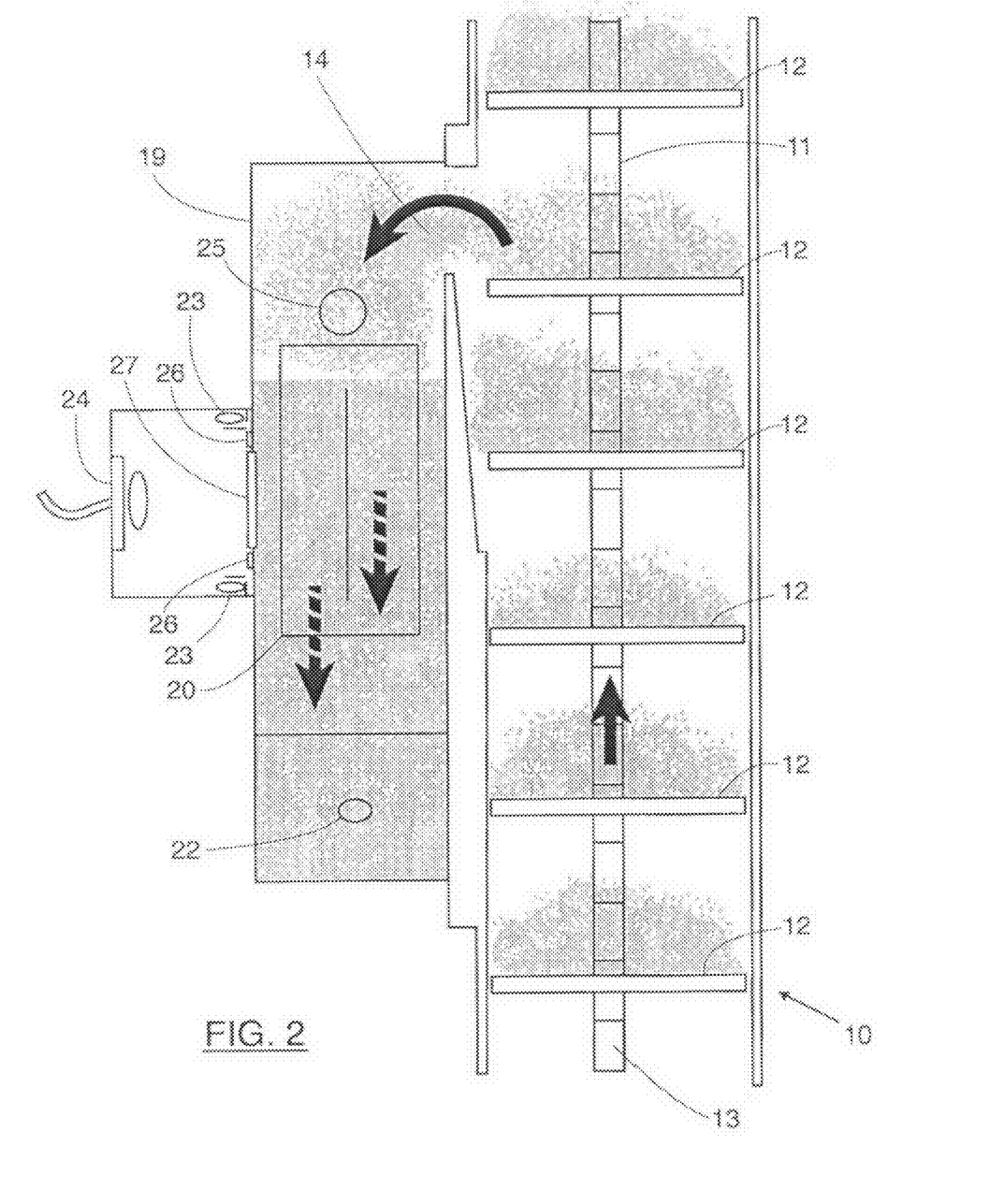
FIG. 2 is a view similar to FIG. 1 rotated through 90°.

As is clear from FIGS. 1 and 2 the paddles 12 in use of the grain elevator 10 travel upwardly along one side of the elevator; and downwardly along the other side. For convenience these sides are referred to herein respectively as the "clean grain elevator up-going side" and the "clean grain elevator down-going side".

The return auger 16 and the housing 19 are represented schematically in FIGS. 1 and 2.

Housing 19 is generally continuous. In the vicinity of auger member 17 housing member 19 is cylindrical.

A drive arrangement such as a motor or transmission 21 is secured to one end of the cylindrical portion of housing 19. A drive shaft 22 extends parallel to the longitudinal axis of the cylindrical portion. Auger member 17 is rigidly secured to drive shaft 22 whereby on activation of the motor or transmission 21 rotation of auger member 17 occurs so as to convey grain upwardly.

The grain entrance 14 and grain exit 18 are defined as apertures in housing 19. As indicated in the drawings, the respective apertures 14 and 18 are so located as to provide for convenient transfer of grain via the auger 16.

The up-going side of clean grain elevator 10, the housing 19 and auger 16 between them define a crop movement path. The crop movement may be continuous or discontinuous (intermittent). In a mode of operation of the apparatus of the invention, the first part of the housing 19 is filled up to a level above the crop sensing area. To this end the housing 19 is provided with a level sensor 25, arranged below the entrance 14. The purpose of the level sensor 25 is to suspend operation of the auger 16, and hence clearing of the sensing area until a complete filling of the bypass occurs. Alternatively, a complete filling of the bypass may also be derived from the images taken by the apparatus of the invention. For instance, the inside of the housing may be of a particular, easily-distinguishable colour. Clearing of the sensing area is not allowed as long as the pixels in the upper sensing area still show this colour, because of the incomplete filling of the housing.

A moisture sensor 20, e.g., a sensor of the capacitive type, may be affixed to a wall of the housing for monitoring the moisture content of the crop material. In order to ensure reliable moisture measurement it is required that the sensor member extends completely into the crop material. This can be verified by the level sensor 25 below the housing entrance 14. The housing may also contain one or more other grain quality sensors, such as a protein, oil or sugar content sensor.

Although every effort is made at the grain cleaning mechanism stage of the combine harvester process to eliminate DOG from the aforementioned crop movement path, in practice this is impossible.

This is partly because some MOG is of similar size and mass to cleaned grains whereby it is readily conveyed with the cleaned grains along the crop movement path. Also some MOG and grains may, depending on their moisture contents, coalesce and adhere to one another. Additionally some MOG, such as dust and straw fibres, are light in weight. The movement of the various internal components of the combine harvester causes air flows that may draw such particles into the crop movement path. A sudden local or general overload of the sieves may also drastically reduce the cleaning capacity of the system, such that a substantial fraction of the MOG is not evacuated from the combine harvester. Also an uneven sieve load may cause poor separation of the MOG, because the air flow through the sieves is redirected to the lightly loaded areas.

For the reasons noted herein, it is desirable to assess the composition of crop in the crop movement path.

Therefore in addition to the various, above-described components of the combine harvester defining a conveyor for crop, the apparatus according to the invention shown in FIGS. 1 to 5 includes a light source represented schematically by numeral 23 in FIGS. 1 to 4. The light source is located to illuminate crop in the crop movement path. In the specific embodiments shown the location of the light source is such as to play light through a glass window 27 onto crop moving in the upright portion of housing 19 of return auger 16 between the grain entrance 14 and the auger member 17. The glass window 27 preferably is treated to be non-reflective, in order to eliminate the effects of stray reflections of light source 23. The crop side of the window should have low adhesive characteristics for the crop and MOG and be sufficiently resistant to scratches. This may be realised by a proper transparent coating.

The apparatus of the invention additionally includes a camera 24 (including a lens) that is arranged to capture sequential images of crop moving in the crop movement path. The images are taken through the glass window 27. The light source 23 may be arranged along the circumference of the window 27 and shine its light on the interior of the box 28 that holds the camera 24. The walls of the box 28 reflect the light and provide a diffuse illumination on the crop material in the housing 19.

Figure 3:
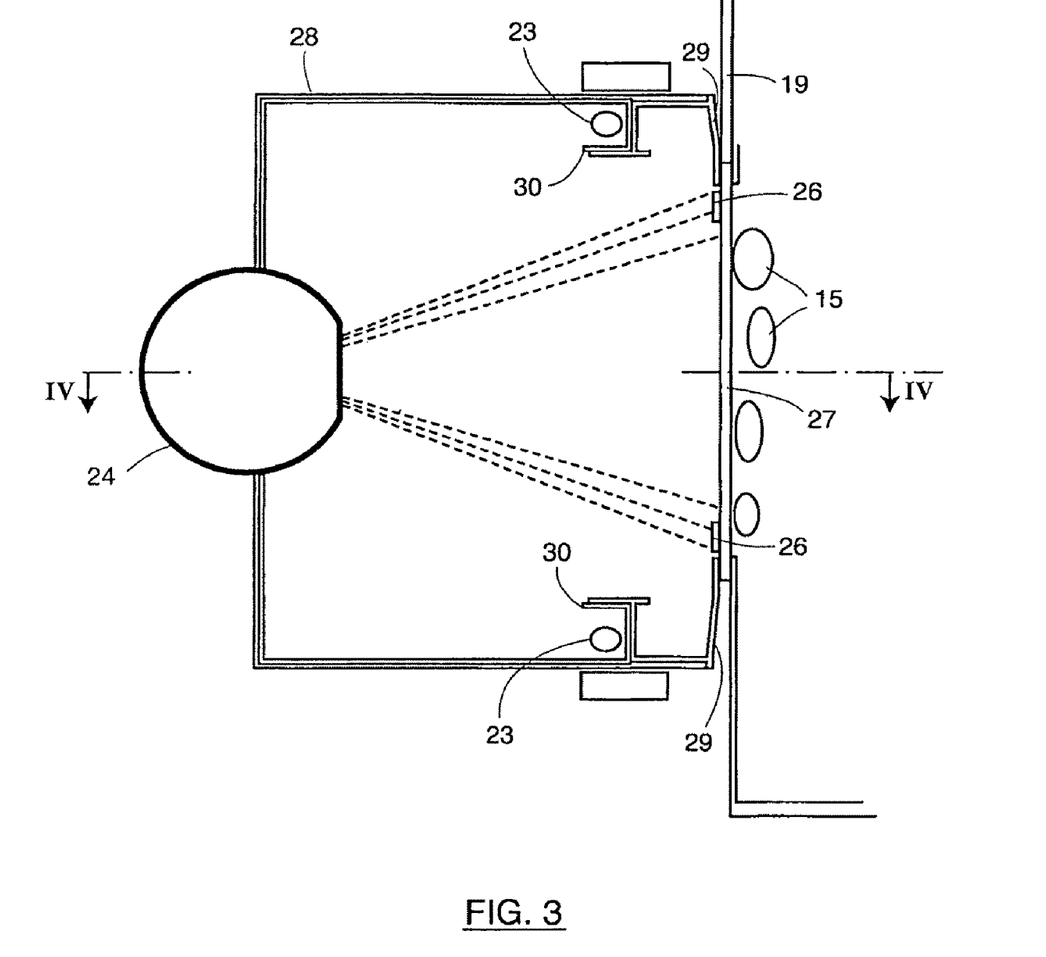
FIG. 3 is a schematic, elevational side view of apparatus according to the invention.
Figure 4:
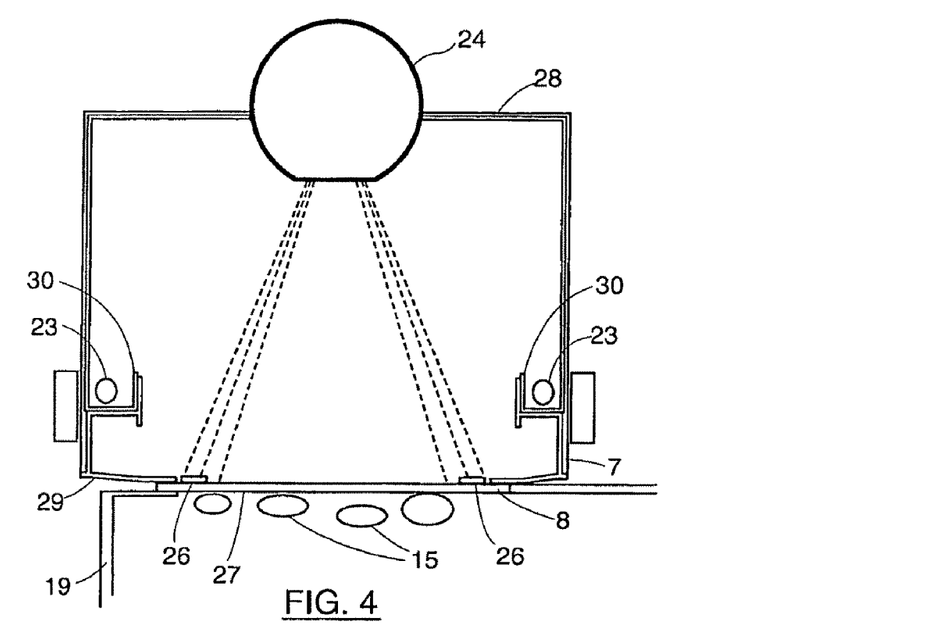
FIG. 4 is a schematic, sectional top view of the apparatus, taken along lines IV-IV of FIG. 3.

In the embodiment shown in FIGS. 3 and 4, the crop analysis apparatus comprises a parallelepiped box 28 having a non-reflective glass window 27, which is mounted by a rubber sealing 29 adjacent the auger housing 19. All along the edge of the window 27, the box has a gutter provided with a range of LEDs, which constitute the light source 23. The LEDs are directed to the interior of the box 28, which is coated with a layer of diffuse reflective paint. The gutter 30 prevents the LEDs from shining directly upon the kernels 15 in the crop sensing area. In this manner the crop material is lighted in a substantially uniform manner. The border of the window has a reference strip 26, whereof the use will be described in further detail hereinafter.

Figure 5:
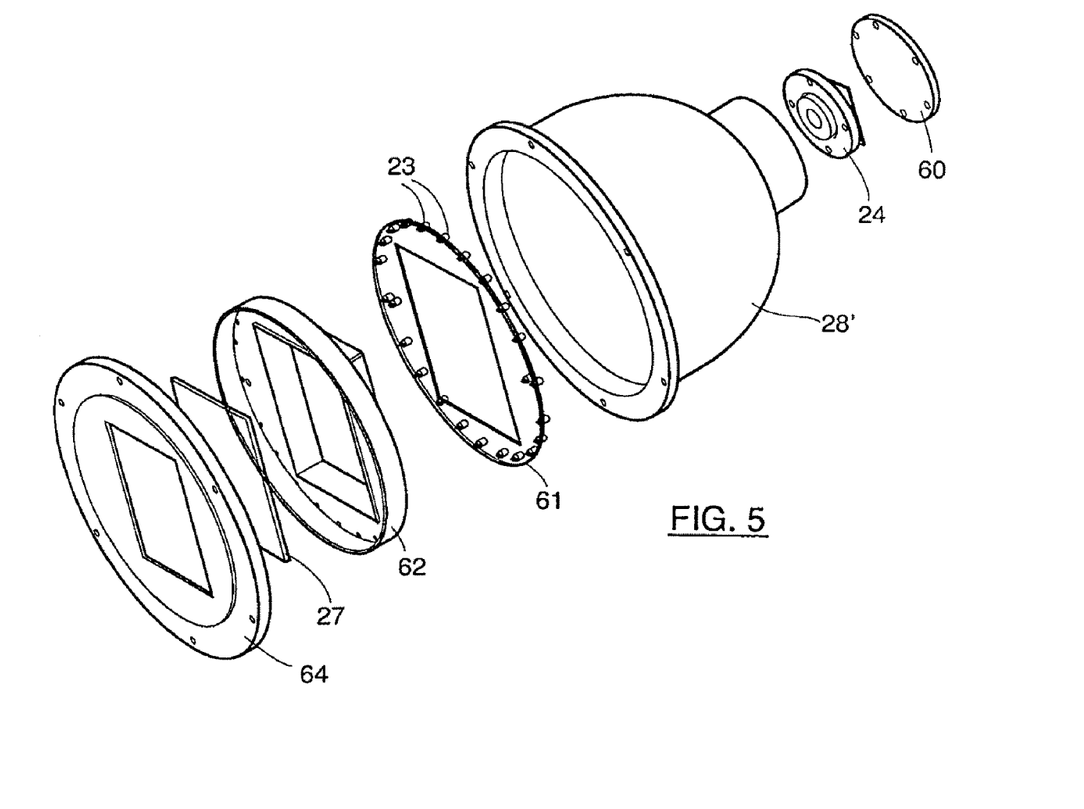
FIG. 5 is an exploded view of another embodiment of apparatus according to the invention.

In the embodiment shown in FIG. 5, the rectangular box has been replaced with a dome-shaped box 28' for even better dispersion of the light. The interior of the dome has a diffusive reflective coating. The camera 24 is mounted to the top of the dome and is held therein by a cover 60. The camera may have a built-in Digital Signal Processor, which is programmable to treat the images captured by the CCD elements. The LEDs of light source 23 are mounted to a printed circuit board 61, which is received in the base of the box 28'. A holding element 62 on the one hand holds the non-reflective glass window 27 and on the other hand retains the board 61 inside the box 28'. The element 62 has a rearwardly extending border for constituting the gutter 30 that shields the LEDs from the window 27. A cover 64 closes the dome-shaped box 28' and thereby secures the window 27, the holding element 62 and the circuit board 61. The apparatus further comprises at least one reference strip (not shown) adjacent an edge of the glass window 27, in the image area of the camera 24.

The box 28 or 28' may be filled with slightly pressurised passive gas, such as nitrogen, in order to prevent the ingress of dust and moisture and to prevent the consequent pollution and condensation, which causes early deterioration of any electronic or other component inside the enclosure of the box.

The apparatus of the invention further includes a control device and a processing device. The control and processing devices are not shown in the figures, but the light source 23, the camera 24, the control device and the processing device are operatively connected together.

The nature of these components is such that the intensity and/or the colour of the light output by the light source is adjustable in dependence on one or more control commands generated by the control device and determined by optical characteristics generated by the processing device of one or more prior images captured by the camera.

In practice in apparatus such as a combine harvester the control and processing devices are embodied as one or more parts of e.g. a central processing unit ("CPU") that carries out numerous functions such as but not limited to the generation of control commands determining the height of the header bar of the combine harvester, the forward speed of the vehicle, the throttle governor setting, the selected transmission ratio, the operation of a discharge conveyor for emptying the clean grain tank, the settings of the opening of the sieves and the speed of the cleaning fan and numerous other functions.

The precise list of tasks carried out by the CPU varies from machine to machine, depending on its level of complexity. It is however generally the case that all "top range" combine harvesters currently on sale incorporate a CPU that typically would be capable of carrying out the processing and control functions described in more detail herein below.

When the apparatus of the invention is embodied for example in a silo, hopper, rail car or tanker, the control and processing devices may be embodied as for example a personal computer that is appropriately programmed and operatively connected to the light source 23 and camera 24.

Regardless of the precise manner in which the apparatus is embodied, the ability of the processing and control devices to adjust the output of the light source in dependence on one or more prior images captured by the camera means that the light source may be of considerably is lower precision and stability than has been proposed in prior art machine vision arrangements for crop analysis.

This in turn means that comparatively unsophisticated components may be employed in the apparatus of the invention.

This is advantageous bearing in mind the harsh environments usually encountered in a crop movement path of the kind described herein.

The use of unsophisticated light sources means that the user of the apparatus of the invention may be unconcerned about the cost of replacing them Alternatively, it may simply be possible to employ components that are robust by reason of their simplicity, thereby conferring a longer useful life on the components than has been available in prior art arrangements.

The apparatus shown in FIGS. 1 to 5 also includes a reference member shown schematically by numeral 26. The reference member is a strip of material whose colour and reflectance properties are known. The reference member 26 is located adjacent the crop movement path such that each image captured by the camera includes at least part of the reference strip.

The processor is programmed so as to assess the colour characteristics of the reference member 26 and generate the aforesaid control commands in dependence on such characteristics.

Including in each image captured by the camera at least part of the reference member allows a comparison between on the one hand the colour properties of the reference member and on the other hand the measured properties of the crop visible in the remainder of the image. The comparison takes place on the basis of emitted light spectra. Assuming the processor to be appropriately programmed, the apparatus of the invention may as a result determine data pertaining to the spectra and intensity of light emitted by the light source. The processor then generates control commands that as necessary adjust the emitted spectra and intensity whereby in respect of the next succeeding image captured by the camera 24 the spectra and intensity are adjusted so as to approach a predetermined set of values. Thus the apparatus of the invention repeatedly corrects for any drift or other errors in the spectra and intensities emitted by the light source or for any changes in camera sensitivity. It follows therefore that there is no need for the light source to comprise high-precision components. The apparatus is also capable of compensating for any drift of the camera components. For instance, a lesser sensitivity to light of a particular wavelength will be compensated by emitting more light of the same wavelength.

In more detail, capturing of data pertaining to the emitted spectra and intensities occurs initially in real-time by reason of the camera 24 capturing light reflected from the reference member 26.

Thereafter the measured intensities recorded in respect of different parts of the reference member 26 are compared with predetermined values constituting a database stored in a memory associated with the processor. Thus even if the supply voltage to the light source 23 is stabilised the apparatus of the invention can compensate for changes in illumination intensity resulting from ageing of the LEDs, malfunctions of one or more LEDs or (most commonly) temperature changes within the clean grain elevator section of the combine harvester.

Further, in more detail, the colour properties of the reference member that form the subject of the aforesaid comparison step include its reflectance at one or more predetermined wavelengths.

In a preferred embodiment of the invention the light source at least includes respective red, green and blue LEDs, the peak outputs of which are approximately at wavelengths of 630 nanometres, 525 nanometres and 472 nanometres. The colour properties of the reference member 26 stored in the database therefore preferably are its reflectance values at these three wavelengths.

In a further embodiment the light source may be supplemented with violet or ultraviolet and near infrared LEDs. For instance, the violet may have a wavelength of 405 nanometres, which can still be captured by conventional CCD cameras, while providing a very clear distinction between the light mass inside a broken grain kernel and the surface of whole grains. The near infrared LEDs may emit light having a wavelengths of 880 and/or 905 nanometres for capturing data relating to moisture and/or sugar content of the crop particles.

As mentioned above, in the preferred embodiment of the invention, the reference member is an elongate strip that in use of the apparatus is aligned with and adjacent an edge of each image captured by the camera 24. An advantageous position is adjacent an edge of the window in the housing 19 through which the camera 24 takes the images of the crop material. The reference member preferably is attached to the crop side of the glass, in order to take account of optical effects the glass may have on the lighting of the crop. However, other forms and positions of reference member 26 are possible within the scope of the invention. Moreover they may be located otherwise than the arrangement described. Such variations will readily occur to those skilled in the art.

Conveniently the colour properties of the reference member 26 are chosen such that its reflectance at certain wavelengths corresponds closely to the reflectance of crop components that are of interest. These include kernels, chaff, straw, broken kernels or different crop types. Contrasts in the captured images should be maximal for these different parts.

The processing device is as noted programmable. In the preferred embodiment of the invention shown it is programmed to carry out one or more of a threshold adjustment; an erosion adjustment; and/or a dilation adjustment on one or more of the images captured by the camera. In practice the processing device is programmed to carry out such adjustments on each image.

As mentioned above in relation to EP-A-0 826 959, the basic principle of threshold adjustment involves the allocation of a certain, predetermined value of reflected light intensity as recorded in respective pixels, as a threshold for discrimination between different types of object in the images captured by the camera 24. In simple terms, all pixels whose intensity value at a certain wavelength is above the threshold is considered to be one type of object (e.g., a contaminant such as chaff); and all pixels having a reflected light intensity at the predetermined wavelength below this value considered to be e.g., grain or another crop.

The processor is in the preferred embodiment of the invention capable of combining the threshold analyses at each of the wavelengths corresponding to red, green and blue (possibly also violet and near infrared) light emitted by the light sources 23. It is however within the scope of the invention for the processor to consider a greater or lesser number of reflected light wavelengths in the pixels if desired.

In EP-A-0 826 959 the threshold value was determined by reference to an "intensity versus number of pixels exhibiting that intensity" graph, for detecting e.g. leaves among harvested grapes.

Such a graph clearly shows two peaks, one of which corresponds to the grapes and the other of which corresponds to the leaves. The processor in EP-A-0 826 959 operated dynamically to determine the threshold reflective light intensity value as an intermediate value, identified as a local minimum, between the two peaks. As a result the threshold measurement was relative and was independent of the absolute intensity of light reflected by the respective crop components.

The water or moisture and sugar content of the grapes assessed in EP-A-0 826 959 was very significantly different from that of the contaminating leaves. Therefore it was comparatively straightforward, in that application, to tag the respective light intensity peaks according to the readings of a moisture sensor operating in conjunction with the camera, light source and processor. In other words, in the case of crop and contaminants having distinct moisture or sugar contents it is easy unambiguously to discriminate between the reflected light intensity levels for the respective components. The difference is most pronounced for wavelengths in the near infrared band.

This step however is considerably more difficult in the case of a machine handling or harvesting grain-type crops. This is not least because for example chaff and grain have very similar water contents. Also the ratio of their reflectance peaks reaches a maximum of 2:1 but most of time is between 1.2:1 and 1.5:1 in terms of reflectance intensity values at wavelengths close to 500 nanometres, as illustrated by the graphs in FIGS. 8 and 9.

Furthermore, in the cleaned grain sections of a combine harvester the percentage of contaminants such as chaff may be only 1% by mass, which corresponds perhaps to only 5% of the area of each image captured by the camera 24. Therefore the overall intensity peak of the MOG in the image is very low.

The foregoing factors combine to make it particularly difficult to use the threshold adjustment method for discriminating between grain and MOG in e.g. a harvesting machine.

In accordance with the invention, the automatic adjustments of the illumination by the light source 23 may advantageously enhance the discrimination between pairs of peak reflectance values under investigation. Following such adjustment therefore the use of a relative threshold determination technique as disclosed in EP-A-0 826 959 is considerably more viable than would otherwise be the case. Thus following such illumination adjustment it is once again possible to determine two distinct peaks in the "intensity versus amount of pixels with that intensity" graph, and thereby dynamically establish a threshold value that is the local minimum between the two peaks.

In addition, within the scope of the invention it is contemplated to sub-divide each captured image into small, equal parts, to which the aforementioned illumination intensity and threshold analysis techniques are respectively applied.

The goal is to increase the traceability of the MOG pixels in the image. Since the overall DOG concentration might be low it would drown in the reflection of the grain for the total image and therefore the peak of the DOG reflection in the reflection frequency graph would be not distinguishable. However, analysis of smaller parts of the total image identifies the parts where MOG is present: for these regions the reflection frequency graph will show, distinctly from the peak corresponding to the grain particles, a substantial peak corresponding to the DOG-related pixels. The automatic peak detection and threshold adjustment described in EP-A-0 826 959 can be applied to each image part showing such peak for identifying the MOG.

It is also possible to perform an adjustment of the illumination for each image part in order to enhance the discrimination of both intensity frequency peaks.

One way of achieving the sub-division of the image would be to use a mechanically actuated (e.g. sliding) shutter or moveable window, that effectively causes each image captured by the camera 24 to be an isolated sub-component of the entire image area. Alternatively and preferably, the sub-division may be carried out as a software technique programmed into the processor.

In addition to the foregoing techniques, it is possible within the scope of the invention as claimed to include image texture analysis.

Figure 10A:
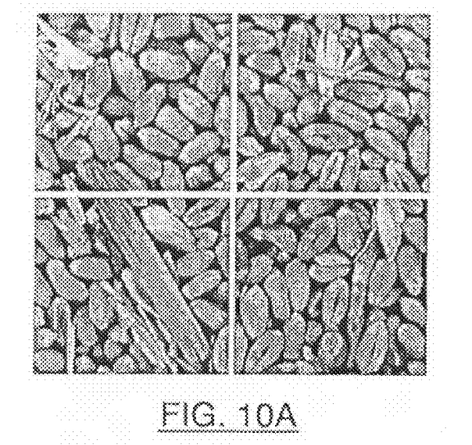
FIG. 10 shows an image of grain and MOG and a Fourier transform of the same.
Figure 10B:
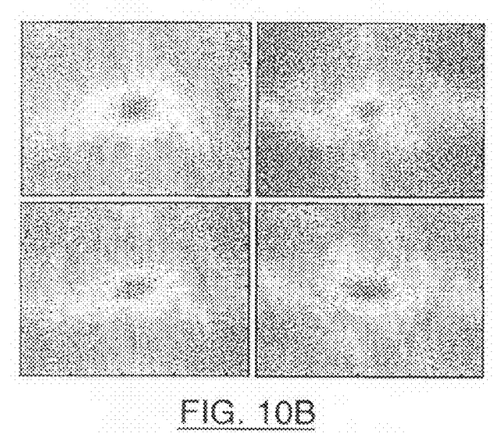
Figure 10C:
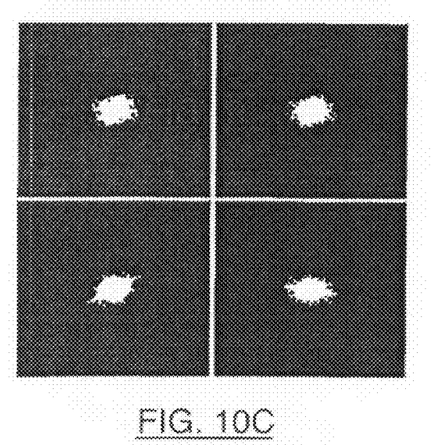

This technique examines the spatial frequency distribution of the reflectance peaks. The transformation to the frequency domain can be done by techniques such as Fourier transformation, Wavelet transformation, etc. FIG. 10A illustrates an image of grain and DOG which is divided into four quadrants. The lower, left hand quadrant contains a straw fragment. FIG. 10B is a representation of the Fourier transform on a logarithmic scale of the FIG. 10A image. Thresholding of the transformed image results in FIG. 10C. The effects of the straw become apparent in each lower left hand quadrant of the image. The deviation from the generally elliptical shape can be used as an indication of the presence of elongate material such as straw.

The adaptive illumination technique of the invention is particularly effective when using texture analysis techniques. As a result of the adaptive illumination method disclosed herein the distribution in the spatial texture spectrum caused by e.g. straw pieces can be selectively enhanced or decreased The analysis of the image by the processing device may also provide data on the mean dimensions of the grain kernels. Such data are useful for later automatic adjustments in the harvesting machine or processing plant. For instance they may be used for adjusting the opening of one or more sieves in a cleaning device.

The erosion and dilation techniques ref erred to herein as forming part of the invention may be complemented with shape analysis and edge detection.

As explained elsewhere in the art, erosion is a technique of disregarding from the analysed parts of an image those pixels whose reflectance levels are "border-line", i.e. in which the detected reflectance level is ambiguous.

Elimination of such pixels from the analysis allows effectively sharper-edged particle images to be obtained. It also eliminates from the image stray small spots, which do not contribute to the succeeding shape analysis or edge detection.

However, the erosion technique simultaneously decreases the size of each particle, as perceived by the processor, compared to its true size value. Dilation techniques are known per se in the art in order to restore the particles, as analysed in the images, to their full sizes. The stray spots that were completely eroded, are not restored.

In accordance with the invention, the processor may in addition to the foregoing steps analyse the particle shapes by looking at e.g. their dimensions.

For example, when the length of a particle exceeds the average grain kernel length by a factor of two, the software programmed into the processor may make an assumption that the particle is a straw particle.

At the same time, the software may search for e.g. rectangular corners in the image of the particle thereby confirming the presence of straw.

Of course the same technique may be readily applied to other types of contaminant (in respect of which the processor would seek to identify other shape and size characteristics).

The use of the adaptive illumination technique of the invention advantageously enhances these aspects of image analysis.

Adjustment of the illumination based upon the characteristics of the image not only compensates for varying properties of the light source (changes of intensity and/or colour) but also for varying properties of the camera (e.g., temperature dependence of the CCD elements in the camera). As harvesters have to work under a wide range of conditions, the systems need to have to a similarly wide operating range.

Figure 6:
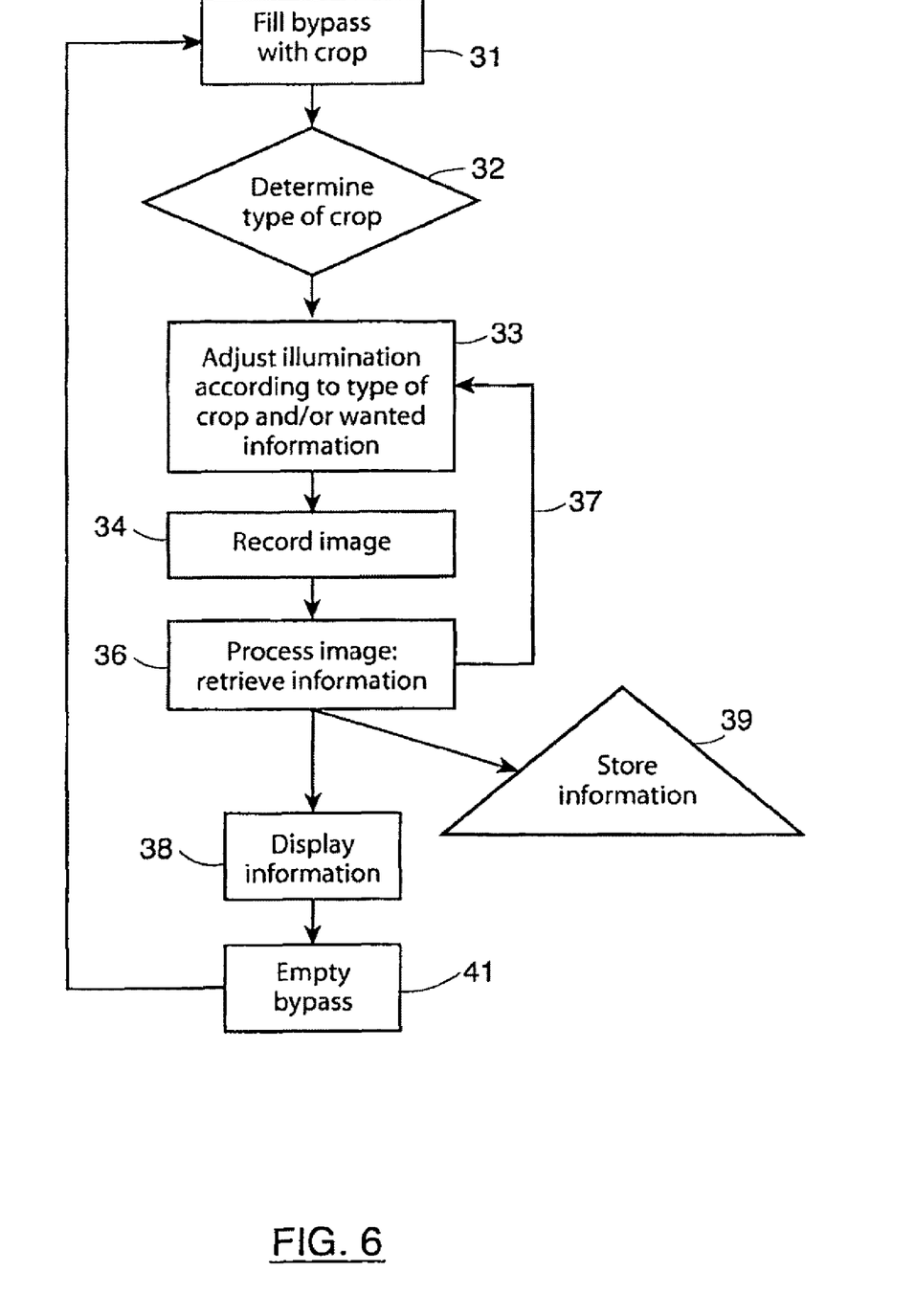
FIG. 6 is a flow chart showing steps in a method according to the invention.

Ref erring now to FIG. 6, there is shown a simple flow chart of method steps in accordance with the invention. The flow chart of FIG. 6 assumes that the software programmed into the processor has already undergone various start-up and test routines that need not necessarily relate directly to the image analysis technique described herein.

At step 31 the crop movement path, which in the specific case of a combine harvester is ref erred to as the "bypass", is filled with crop e.g. through use of the paddle conveyor 11 described hereinabove, while auger motor 21 is halted. Filling of the bypass will be indicated by the level sensor 25.

At decision box 32 the type of crop is determined. Such a determination may result e.g. from data input by the combine harvester operator; or it may result from an initial image and moisture content analysis carried out by the processor, or another type of initial analysis. The second method may involve comparison of one or more characteristics (colour, intensity, size, shape, moisture, etc.) with a look-up table of standard values for each crop type Regardless of the precise way of determining the crop type the next step in the process, at step 33, is to adjust the illumination output by the light source 23 (in each of the wavelengths corresponding at least to red, green and blue light) to a mean or initial level previously determined to be suitable for illuminating crop of the type identified.

A suitable illumination may be one maximising the differences in reflection between the grain and MOG. For a particular crop, appropriate wavelengths may be derived from a reflection graph such as FIG. 8, which was established for a wheat variety. A suitable illumination may also be one maximising the differences in the ratio of reflection between the grain and MOG, as shown in FIG. 9 for the reflections of FIG. 8. It is also envisageable to capture images at various wavelengths and to add, subtract, divide or multiply the resulting reflectance values for each pixel in order to enhance the discrimination between grain and MOG.

The illumination may now be optimised for the crop contents of the housing 19, by applying a variation to the illumination, e.g., by changing the intensity of the LEDs of one colour, and capturing a new image. Next, the processing device analyses the effect of this variation on the distribution of the reflectance values in the image or of the calculated values derived therefrom. If the discrimination between the peaks representative of grain and MOG is better, the illumination is varied in the same direction and a new image is captured and analysed. If the analysis proves that the discrimination is improved, the intensity variation will go on in the same sense, until the discrimination results start to get worse. If the first variation has a worse discrimination for result, the variation is reversed, which should yield a better effect. The changes are repeated in the same, reversed sense until the analysis of the captured images shows that discrimination is not getting better or is worsening. The variation is halted here. In this manner it is possible to tune the illumination for the selected colour. The process may take about five iterations for determining the optimal lighting. This procedure may be repeated for each available colour or for each colour which is deemed relevant for the identified crop type or for the screened MOG type (e.g., detection of broken grain kernels).

After having established the optimal illumination, the camera 24 records the first of a sequential series of images of crop in the crop movement path, as signified at step 34 of the flow chart.

Step 36 represents the steps of image processing described hereinabove.

Arrow 37 represents iterative looping of the control programme in order to capture the previously-mentioned sequential series of crop images corresponding to movement of crop in the crop movement path over time, and/or to the capturing of a series of sub-component images as aforesaid.

Either simultaneously, or in a caching mode, the processor may display data and/or images as represented at step 38; and may store data, as represented at step 39, in a memory device operatively connected to the processor.

After emptying the bypass by operation of the auger motor 21, as represented at step 41, the routine loops back to the bypass filling step at step 31.

Figure 7:
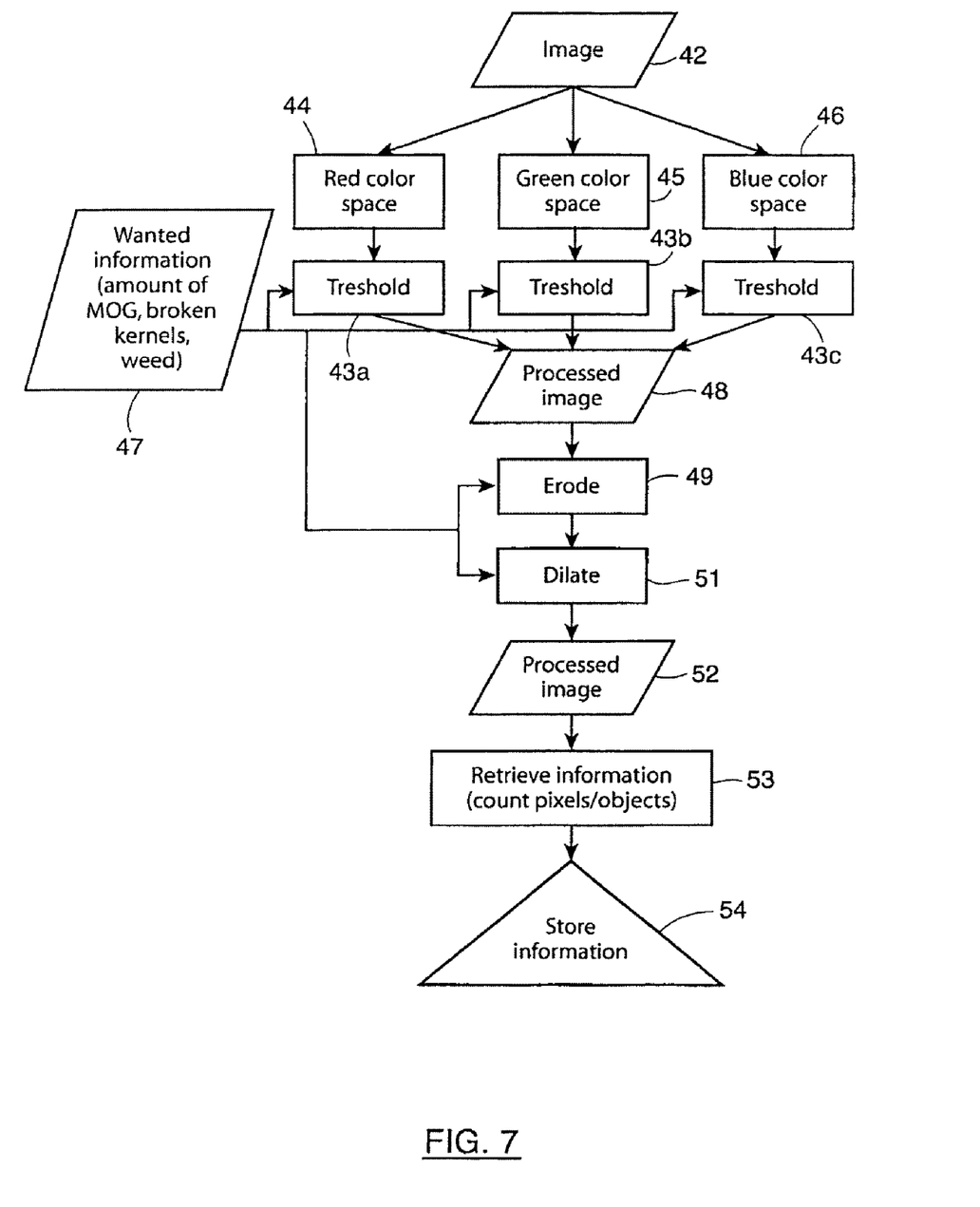
FIG. 7 is a further flow chart showing method steps according to the invention.

FIG. 7 shows the process steps carried out at step 36 of FIG. 6 in more detail.

For each image 42 a respective threshold analysis 43*a*, 43*b*, 43*c* is carried out in respect of each of the red, green and blue reflected light components 44, 45 and 46.

The required information as represented by step 47 is an input to each threshold analysis 43*a*, 43*b*, 43*c* the result of which is an intermediate, processed image 48.

Erosion and dilation techniques 49, 51, as described hereinabove, result in a final processed image 52 from which the desired image information can be extracted (step 53) for example through counting the number of pixels having a predetermined characteristic; through object identification as described herein or any of a range of other techniques for establishing the content of the crop captured in each image.

In the example of FIG. 7 the final step in the sub-routine (step 54) is that of storage of information. Of course as indicated in FIG. 6 the data may alternatively or additionally be displayed.

When the system finds that the MOG content or a portion thereof (e.g., the straw of chaff content) exceeds a predetermined limit, an audible and/or visible alarm may be generated for warning the operator about the unacceptable grain quality and giving him the opportunity to take corrective measures. These may include changes to the harvester settings and the travelling speed. The system can also be used to identify unallowable grain contaminants in the captured images.

The information on the grain and MOG content as provided by the processing device can be used by the same processing device for validating or adjusting the signal or data provided by other grain quality sensors, such as the moisture sensor 20 or the protein, oil or sugar content sensor. For instance, if the percentage of MOG in the image exceeds a predetermined limit, the processing device may be programmed not to use or store the signals provided by these sensors. The monitoring may be resumed as soon as the processing device finds that the MOG content has come back to acceptable levels. If the MOG percentage is at a lower, but still significant level, the MOG data can be used for adjusting the provided quality signals, such that they relate only to the grains themselves.

Figure 8:
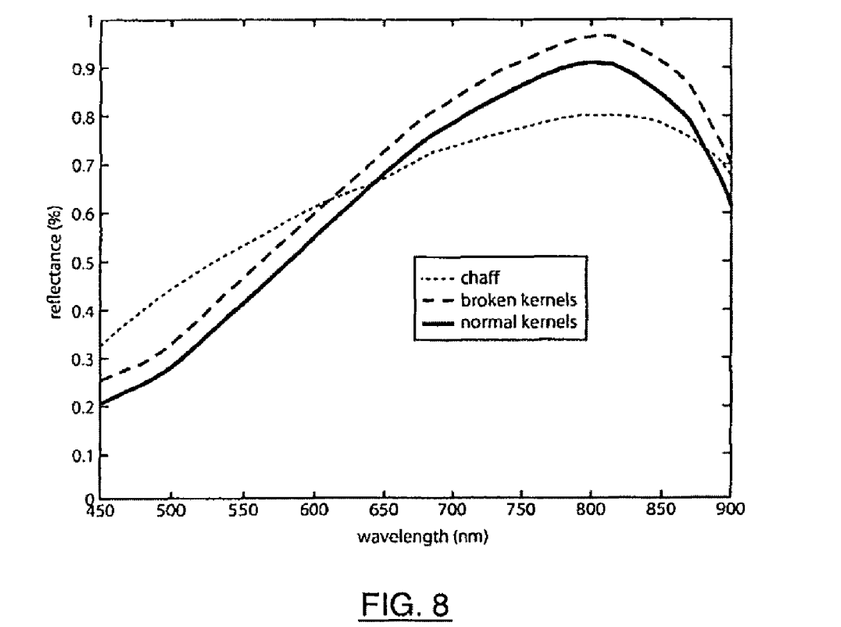
FIG. 8 is a graph showing the reflectance spectrum of grain, broken grains and chaff in crop conveyed to a combine harvester.
Figure 9:
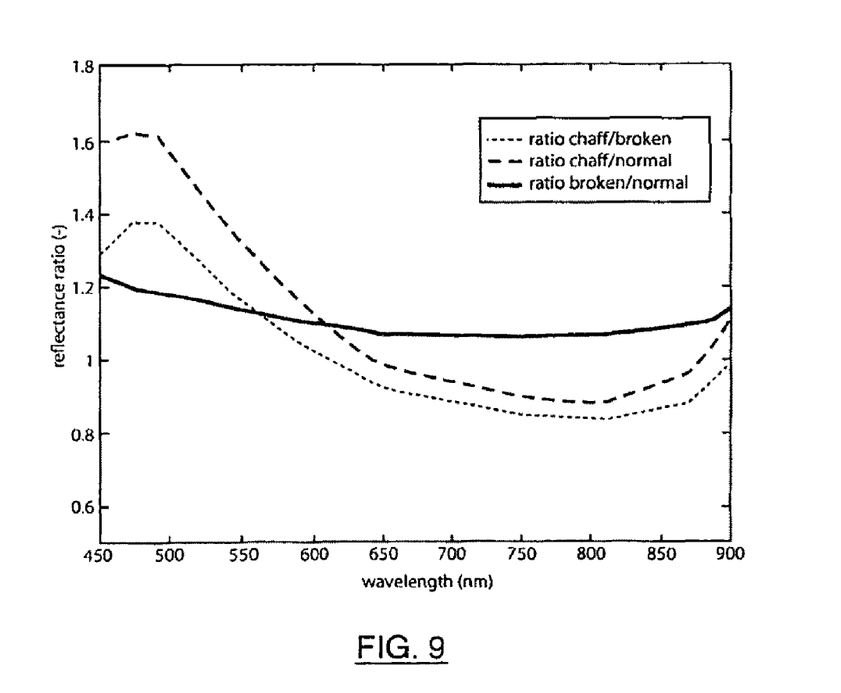
FIG. 9 is a graph showing the reflectance ratios for the crop components of FIG. 8.

For completeness FIGS. 8 and 9 show the difficulty in distinguishing between chaff, broken kernels and normal kernels based solely on reflectance measurements (i.e. without practising the method steps of the invention). As noted, over virtually the entire range of visible wavelengths the reflectance differences between the three crop components are small, thereby confirming that in the absence of the apparatus and method of the invention it would be extremely difficult to carry out effective discrimination techniques. If the intensity and the colour of the light source cannot be controlled within a small range, the image might change to an extent beyond the available reflectance differences for various crops and contaminants. This would render the image analysis unreliable and severely impact the automatic harvester routines which are based on this analysis.

The invention has been described with respect to crop material samples taken from the clean grain elevator in order to assess the quality of the grain that is fed into the grain tank. However, it can also be used for analysing the crop material at other locations of the harvesting machine. For instance, it is advantageous to know the composition of material in the return system of a combine harvester, i.e. the crop path which takes incompletely threshed and/or cleaned crop material at the end of the upper sieve, rethreshes it and feeds it back to the front of the cleaning system. A control system can use the data on the composition of this material for real-time adjustment of the air flow of the cleaning fan, the opening of the sieves or the setting of a threshing or rethreshing drum and concave. The monitoring apparatus can be installed on a return auger or return elevator which feeds return material from a trough below the sieves to the front of the threshing and cleaning system.

The apparatus can also be used for automatically identifying the harvested crop or variety. This information can then be used by the processing device for automatic pre-adjustment of various harvester settings, such as threshing drum speed, concave, fan and sieve opening setting, etc.

The invention claimed is:

1. Apparatus for analysing the composition of crop in a crop-conveying machine, the apparatus comprising:
   a conveyor for conveying crop in the machine, the conveyor comprising a portion defining a crop movement path;
   a light source that illuminates crop in the crop movement path;
   a camera that captures sequential images of crop in the crop movement path;
   a control device; and
   a processing device all operatively connected together, at least one of the intensity and the colour of light output by the light source being adjustable in dependence on at least one control command generated by the control device and determined by optical characteristics generated by the processing device of at least one prior image captured by the camera, wherein the processing device is configured for measuring the reflectance of each element of the image at least two wavelengths and carrying out at least one of an addition, a subtraction, a multiplication, and a division of the measured reflectance values of each image element for better discrimination between crop components, wherein the apparatus further comprises a reference member, the colour properties of which are known, located in or adjacent the crop movement path so as to appear in the images captured by the camera, the processor being capable of assessing the colour characteristics of the reference member and in dependence thereon generating the aforesaid control commands.

2. A method of analysing the composition of crop in a crop-conveying machine, the method comprising the steps of:
   causing the crop to move along a crop movement path;
   illuminating the crop in the path by means of an adjustable source of illumination;
   operating a camera to capture a series of real time images of the crop; and
   operating a processing device to cause adjustment of the illumination source in dependence on at least one optical characteristic of at least one prior image of the crop captured by the camera,
   wherein operating a processing device further comprises the step of:
   measuring the reflectance of each element of the image at least two wavelengths and carrying out at least one of an addition, a subtraction, a multiplication, and a division of the measured reflectance values of each image element for better discrimination between crop components, wherein the method further comprising a step of carrying out a threshold adjustment, by detecting the grey level of each pixel of an initial image containing no grain and allocating to it an extreme grey level depending on a comparison of its grey level to a predetermined threshold value.

3. Apparatus according to claim 1, wherein the known colour properties of the reference member (26) include its reflectance at least one predetermined wavelength.

4. Apparatus according to claim 1, wherein the light source includes respective red, green and blue LEDs.

5. Apparatus according to claim 4, wherein the wavelengths of the peak outputs of the respective LEDs are approximately 630 nm, 525 nm and 472 nm.

6. Apparatus according to claim 4, wherein the predetermined wavelength include three respective wavelengths corresponding generally to the peak wavelength outputs of the red, green and blue LEDs respectively.

7. Apparatus according to claim 4, wherein the light source further includes at least one of respective violet, ultra-violet, and near-infrared LEDs.

8. Apparatus according to claim 7, wherein the wavelengths of the peak outputs of further respective LEDs are approximately 405, 880, and 905 nm.

9. Apparatus according to claim 1, wherein the reference member (26) is an elongate strip that in use of the apparatus is aligned with and adjacent an edge of each image captured by the camera.

10. Apparatus according to claim 1, wherein the processing device is programmable and is programmed to carry out at least one of:
    a threshold adjustment;
    an erosion adjustment; and
    a dilation adjustment
    on at least one image captured by the camera.

11. Apparatus according to claim 1, wherein the camera of which is so located as to capture images of crop moving in the clean grain elevator of a combine harvester, whereby the elevator defines the crop movement path.

12. Apparatus according to claim 1, further comprising a housing including the camera and having formed therein a window permitting light reflected from crop moving in the crop movement path to impinge on the camera for the capturing of the images.

13. Apparatus according to claim 12, wherein the housing includes the light source, the light from which illuminates the crop via the window.

14. Apparatus according to claim 1, further comprising at least one moisture sensor, a protein sensor, an oil content sensor, and a level sensor operatively connected to the processing device.

15. Apparatus according to claim 14, wherein the processing device is programmed to use data from the captured image for at least one of validating and adjusting the output from at least one of the moisture sensor, the protein sensor, and the oil content sensor.

16. Apparatus according to claim 1, further comprising a display device operatively connected to the processing device and located so as to be visible to an operator.

17. Apparatus according to claim 16, wherein the processing device is programmable and is programmed to cause the display device to display at least one of at least one image captured by the camera, at least one image processed by the processing device, and a combination of images.

18. Apparatus according to claim 17, wherein the processing device causes the display device to display the images sequentially in real time.

19. Apparatus according to claim 17, wherein the processing device causes the display device to display the images following at least one of:
    a threshold adjustment;
    an erosion adjustment; and
    a dilation adjustment carried out on each image.

20. Apparatus according to claim 17, wherein the processing device generates at least one command causing the display device to display data pertaining to the composition of the crop.

21. Apparatus according to claim 1, wherein the portion defining a crop movement path comprises a bypass.

22. A method according to claim 2, further comprising a step of dividing each image into a plurality of image portions; and separately processing each image portion.

23. A method according to claim 2, further comprising a step of causing the processing device to discriminate between different crop types based on data in the captured image.

24. A method according to claim 2, wherein the step of operating a processing device to cause adjustment of the illumination source includes the step of comparing the optical characteristics of a reference member (26) with optical characteristics of crop captured in at least one prior image.

25. A method according to claim 2, wherein the step of illuminating the crop further includes illuminating the crop by means of each of a red, a green and a blue light source.

26. A method according to claim 25, wherein the wavelengths of the peak outputs of the respective light sources are approximately 630 nm, 525 nm and 472 nm.

27. A method according to claim 25, wherein the step of illumination the crop further includes illuminating the crop by means of at least one of a violet, ultra-violet, and a near-infrared light source.

28. A method according to claim 27, wherein the wavelengths of the peak outputs of the respective further light sources are approximately 405, 880, and 905 nm.

29. A method according to claim 25, wherein the step of operating a processing device to cause adjustment of the illumination source further includes respective adjustment, as necessary, of each respective light source.

30. A method according to claim 2, further comprising a step of displaying at least one image via a display device.

31. A method according to claim 2, further comprising a step of displaying data characteristic of the crop moving in the crop movement path via a display device.

32. A method according to claim 2, further comprising the steps of carrying out at least one of
 a threshold adjustment;
 an erosion adjustment; and
 a dilation adjustment
on at least one image captured by the camera.

33. A method according to claim 2, further comprising a step of carrying out a texture analysis on at least one image.

34. A method according to claim 33, wherein the step of carrying out a texture analysis includes carrying out at least one of a Fourier transform (10B), and a wavelet transform in order to reference the image to the frequency domain.

35. A method according to claim 2, further comprising a step of using data derived from the captured image for at least one of validating, and adjusting the output from at least one of the moisture sensor, the protein sensor, and the oil content sensor.

36. A method according to claim 2, including the step of automatically carrying out the threshold adjustment.

37. A method according to claim 36, wherein the step of automatically carrying out the threshold adjustment includes recording the number of pixels of the initial image having a predetermined grey level;
 establishing from the recording two peak greyscale values; and establishing a minimum value that defines the threshold from the peak values.

* * * * *